(12) United States Patent
Wieczorek et al.

(10) Patent No.: US 8,774,474 B2
(45) Date of Patent: Jul. 8, 2014

(54) HEART SEGMENTATION IN CARDIAC REST AND STRESS IMAGING

(75) Inventors: Herfried K. Wieczorek, Aachen (DE); Rolf Dieter Bippus, Lemiers (NL)

(73) Assignee: Koninklijke Philips N.V., Eindhoven (NL)

( * ) Notice: Subject to any disclaimer, the term of this patent is extended or adjusted under 35 U.S.C. 154(b) by 435 days.

(21) Appl. No.: 13/203,515

(22) PCT Filed: Feb. 9, 2010

(86) PCT No.: PCT/IB2010/050582
§ 371 (c)(1),
(2), (4) Date: Aug. 26, 2011

(87) PCT Pub. No.: WO2010/109343
PCT Pub. Date: Sep. 30, 2010

(65) Prior Publication Data
US 2012/0033864 A1 Feb. 9, 2012

Related U.S. Application Data

(60) Provisional application No. 61/162,696, filed on Mar. 24, 2009.

(51) Int. Cl.
*G06K 9/00* (2006.01)
*G06T 7/00* (2006.01)
*A61B 5/055* (2006.01)
*A61B 6/03* (2006.01)
*A61B 6/00* (2006.01)

(52) U.S. Cl.
CPC ............... *G06T 7/0081* (2013.01); *A61B 5/055* (2013.01); *G06T 2207/30048* (2013.01); *G06T 2207/10108* (2013.01); *A61B 6/03* (2013.01); *A61B 6/541* (2013.01); *A61B 6/037* (2013.01); *A61B 6/00* (2013.01); *G06T 2207/30101* (2013.01)
USPC .......................................................... 382/128

(58) Field of Classification Search
USPC ................... 382/107, 128, 131, 173; 128/922
See application file for complete search history.

(56) References Cited

U.S. PATENT DOCUMENTS 6,473,636 B1 * 10/2002 Wei et al. ....................... 600/436
6,917,826 B2 * 7/2005 Wei et al. ....................... 600/407
(Continued)

FOREIGN PATENT DOCUMENTS

WO 2008010227 A2 1/2008

OTHER PUBLICATIONS

Kiat, H., et al.; Comparative Feasibility of Separate or Simultaneous Rest Thallium-201/Stress Technetium-99m-Sestamibi Dual-Isotope Myocardial Perfusion SPECT; 1994; The Journal of Nuclear Medicine; 35(4)542-548.

(Continued)

*Primary Examiner* — Phuoc Tran

(57) ABSTRACT

A patient (14), at rest, is injected with a first isotope tracer. After a first uptake period, the patient is stressed and injected with a second isotope tracer. After a second isotope tracer uptake period, first and second isotope imaging data are concurrently detected by data acquiring devices (16). The first and second isotope imaging data are reconstructed into a first or rest state image, a second or stressed state image, and optionally a combined first and second isotope image. The image with the better image statistics is segmented to generate segmentation parameters, which segmentation parameters are applied to both the first or rest and second or stressed state images. In this manner, an image whose image statistics may be too weak for accurate segmentation is accurately segmented by generating two inherently aligned images and applying the same segmentation parameters to both.

14 Claims, 2 Drawing Sheets

(56) References Cited

U.S. PATENT DOCUMENTS

Figure 1:
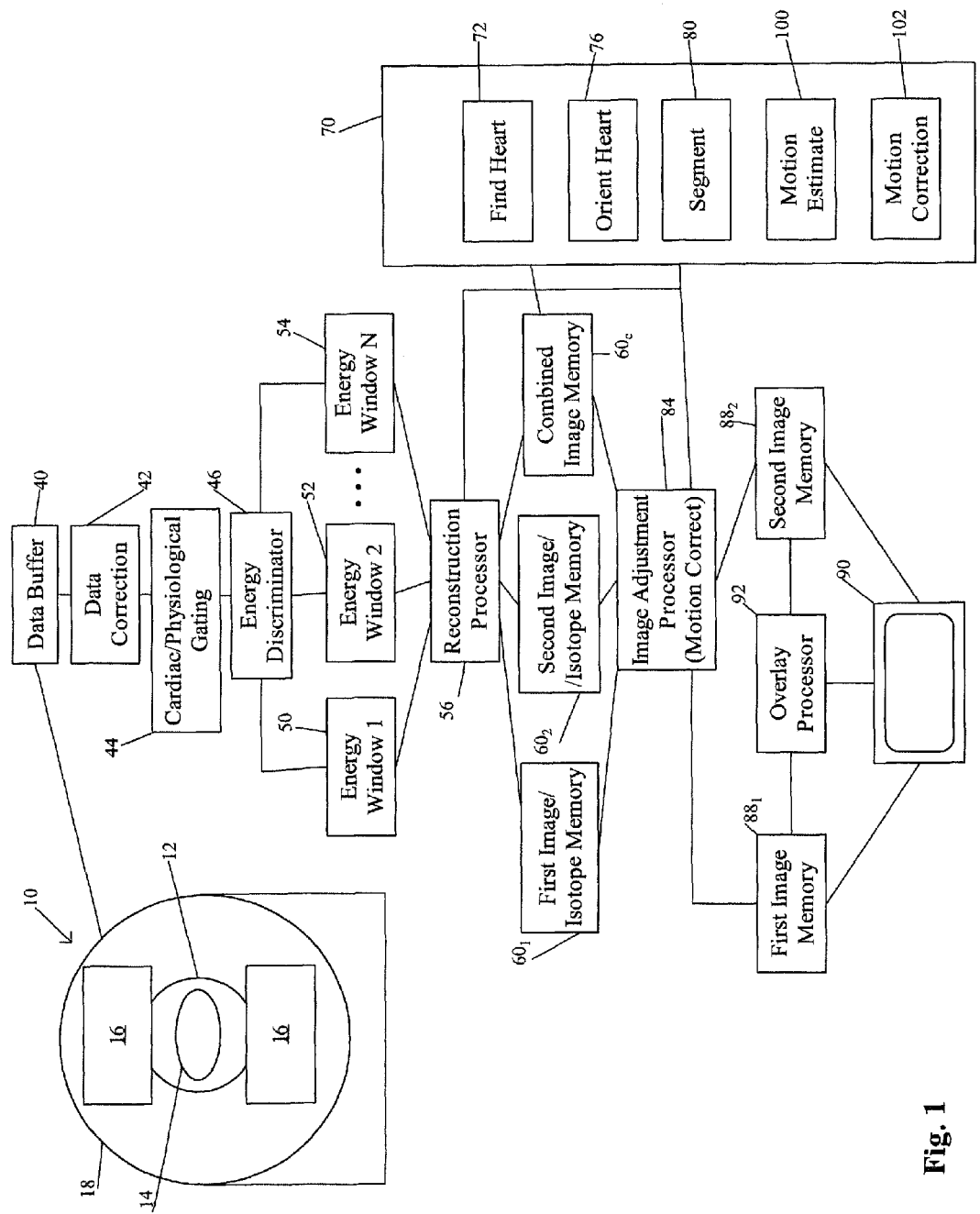

| | | | |
|---|---|---|---|
| 8,000,773 B2* | 8/2011 | Rousso et al. | 600/436 |
| 2008/0033291 A1 | 2/2008 | Rousso et al. | |
| 2008/0226149 A1 | 9/2008 | Wischmann et al. | |
| 2008/0292165 A1 | 11/2008 | El Fakhri et al. | |
| 2010/0142774 A1* | 6/2010 | Ben-Haim et al. | 382/128 |

OTHER PUBLICATIONS

Nakamura, M., et al.; Feasibility of Simultaneous Stress 99mTc-Sestamibi/Rest 201Tl Dual-Isotope Myocarcial Perfusion SPECT in the Detection of Coronary Artery Disease; 1999; Journal of Nuclear Medicine; 40(6)895-898.

* cited by examiner

HEART SEGMENTATION IN CARDIAC REST AND STRESS IMAGING

CROSS REFERENCE TO RELATED APPLICATIONS

This application claims the benefit of U.S. provisional application Ser. No. 61/162,696 filed Mar. 24, 2009, which is incorporated herein by reference.

The present application relates to dual isotope and/or dual tracer imaging. It finds particular application in conjunction with dual isotope SPECT imaging of the heart and will be described with particular reference thereto. However, it is to be appreciated that the present concept is also applicable to other imaging modalities and the imaging of other portions of the anatomy.

Cardiac rest and stress images are typically taken in separate SPECT image acquisition steps. Diagnosis is performed by comparing the two images, typically after automatic segmentation of the heart images.

Technetium (Tc) based tracers have good image statistics and are amenable to segmentation operations. In one protocol, a Tc image is generated at one of the rest and stress states and a second Tc image is generated at the other. However, because Tc is relatively slow to wash out, it is typical to wait 4 or more hours between the rest and stress imaging sessions. This not only slows patient throughput, but also creates stress and rest image alignment issues.

In another protocol, a thallium (Tl) image is generated in the rest state followed by a technetium (Tc) image in the stress state. This has the disadvantage that two scans, each on the order of 15-25 minutes, are performed, reducing the patient throughput. Moreover, Tl images have low statistics, making segmentation difficult and potentially inaccurate, which can have an adverse affect on image interpretation.

In another protocol, the Tc image is generated first, followed by the Tl image. This protocol has similar drawbacks to the protocol in which the Tl image is generated first, followed by the Tc image. Additionally, because the Tc washes out slowly, there is residual Tc in the patient during the Tl data acquisition. The Tc, which has a higher energy, gives up a portion of its energy when it is scattered. This raises the potential for Tc to be downscattered to the same energy as Tl, making the two difficult to distinguish.

The present application contemplates a new and improved system and method which overcomes the above-referenced problems and others.

In accordance with one aspect, a method of diagnostic imaging is provided. First and second isotope imaging data are concurrently acquired from a first isotope tracer taken up by a subject in a first state and a second isotope tracer taken up by a subject in a second state. The acquired isotope imaging data are reconstructed to generate a first state image from the first isotope imaging data and a second state image from the second isotope imaging data. Both the first and second state images are segmented based on a one of the first and second state images or a combined first and second isotope image which has better image statistics. The segmented first and second state images are concurrently displayed.

In accordance with another aspect, a computer-readable medium is provided, which medium carries software for controlling the computer to perform the following steps. Concurrently acquired first isotope imaging data and second isotope imaging data are reconstructed, respectively, into a first isotope image depicting an uptake of a first isotope tracer injected into a subject and a second isotope image depicting an uptake of a second isotope tracer injected into the subject after a first isotope tracer uptake period after injecting the first isotope tracer and a second isotope tracer uptake period before concurrently acquiring the first and second isotope imaging data. A one of the first and second isotope images which has better image statistics or an image reconstructed from both the first and second isotope imaging data is segmented to generate segmentation parameters. The segmentation parameters are applied to each of the first isotope image and the second isotope image.

In accordance with another aspect, a diagnostic imaging system is provided. A reconstruction processor reconstructs concurrently acquired first isotope imaging data into a first isotope image depicting an uptake of a first isotope tracer injected into a subject and second isotope imaging data into a second isotope image depicting an uptake of a second isotope tracer injected into the subject after a first isotope tracer uptake period after injecting the first isotope tracer and a second isotope tracer uptake period before the concurrently acquiring of the first and second isotope imaging data. A segmenting processor segments one of the first and second isotope images which has better image statistics or an image reconstructed from both the first and second isotope imaging data to generate segmentation parameters. An image adjustment processor applies the segmentation parameters to each of the first and second isotope images to generate a segmented first isotope image and a segmented second isotope image. A display concurrently displays the segmented first and second isotope images.

One advantage resides in inherent alignment of the data from the different isotopes/tracers.

Another advantage resides in improved patient throughput.

Still further advantages and benefits will become apparent to those of ordinary skill in the art upon reading and understanding the following detailed description.

The innovation may take form in various components and arrangements of components, and in various steps and arrangements of steps. The drawings are only for purposes of illustrating the preferred embodiments and are not to be construed as limiting the invention.

Figure 2:
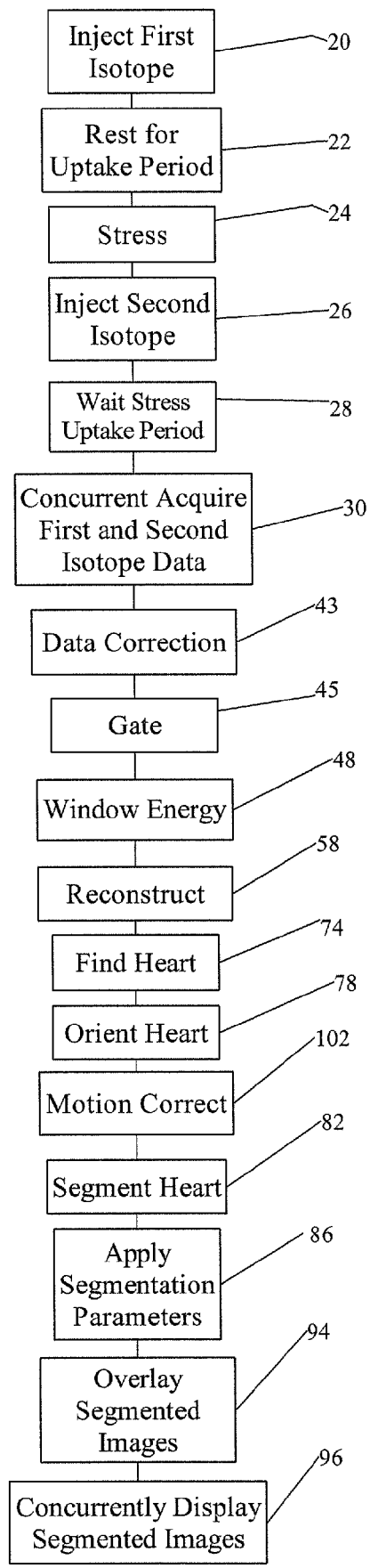

FIG. 1 is a diagrammatic illustration of a diagnostic imaging system in accordance with the present concept; and, FIG. 2 illustrates a method of use.

With reference to FIG. 1, a diagnostic imaging apparatus 10, such as a SPECT imaging system, has an imaging region 12 configured to receive a portion of a subject 14 to be imaged. Imaging data acquiring devices 16 are mounted on the gantry to acquire isotope imaging data. In the illustrated embodiment, the diagnostic imaging system is a SPECT system in which the imaging data acquiring devices include one or more SPECT or nuclear cameras 16, which are mounted to a gantry 18 for rotation around the subject 14. Other imaging systems are also contemplated, such as PET, combined PET or SPECT CT, combined PET or SPECT MR, or the like.

With reference to FIG. 2, in a myocardial perfusion imaging (MPI) embodiment for the detection of coronary artery disease (CAD), by visualization of ischemic regions in the myocardium, the subject, at rest, is injected 20 with a Tc isotope tracer. As is discussed below, other isotopes are also contemplated. The patient remains at rest 22 for a rest or first isotope uptake duration, e.g., 30-60 minutes. The subject is then stressed 24 and a Tl isotope tracer is injected 26. As discussed below, the second tracer may include other isotopes. After waiting 28 for a stress or second isotope uptake duration, typically about 15-30 minutes, the scanner 10 commences concurrently acquiring imaging data 30 from both isotopes.

The concurrently acquired first and second isotope imaging data and, optionally, gating information, are stored in an imaging data buffer 40. A correction processor 42 performs a correction step 43 to optionally correct for one or more of attenuation, scatter, spatial resolution, cross-contamination, and the like. Optionally, a cardiac or physiological gating processor algorithm program or other means 44 gates or sorts 45 the data by a cardiac or physiological phase of the subject. An energy discriminator 46 performs an energy windowing operation 48 to separate the imaging data corresponding to multiple energy windows. Other energy windows may also be used to measure attenuation properties of the subject, measure background scatter, or the like. The energy window data is stored in separate energy window memories.

One or more reconstruction processors 56 reconstruct 58 the imaging data from one or more of the energy window memories. The resultant reconstructed images are stored in a first image/isotope memory $60_1$, a second image/isotope memory $60_2$, and a combined isotope image memory $60_C$, respectively. The reconstruction processor can perform attenuation, scatter, and collimator response corrections. In one embodiment, data from multiple or all energy windows are simultaneously reconstructed, inherently performing the attenuation, scatter, and collimator response corrections. In another embodiment, each isotope image is reconstructed from an isotope specific subset of energies iteratively in separate steps performing the attenuation, scatter, and collimator response connection. In yet another embodiment, reconstruction is performed in separate steps for each isotope's image on an isotope specific subset of the energy windows.

One or more processors 70 include a heart finding processor, algorithm, program, or other means 72 for finding 74 the subject's heart in the reconstructed images. The processor 70 operates on the image with the strongest statistics. When the first and second isotopes are Tc and Tl, Tc typically has the best statistics. In the alternate embodiment in which a combined image is generated, the processor 70 can operate on the combined image. Because the data for an isotopes is acquired concurrently, all images are inherently aligned, commonly scaled, and the like. A reorientation processor, program, algorithm, or other means 76 calculates from the image with the best noise statistics reorientation parameters 78 which reorient main axes of the heart into alignment with preselected directions or axes. For example, the left ventricle is oriented with a vertical axis. The processor 70 further includes a processor, program, algorithm, or other means 80 which segments 82 the reoriented heart image with the best noise statistics. One or more image adjustment processors, algorithms, programs, or other means 84 apply 86 the segmentation parameters, reorientation parameters, and the like to each of the Tc and Tl images to generate aligned and commonly segmented Tc and Tl images which are stored, respectively, in a first image memory $88_1$ and a second image memory $88_2$.

More specifically, segmenting the image with the best noise statistics can be done automatically, manually, or with a combination of the two. During segmentation, regions of the image corresponding to selected structures, e.g., the heart, the left ventricle, the aorta, the liver, or the like, are segmented, e.g., outlined to define the region of the image corresponding to each cardiac physiological structure or region. Once the image with, the best noise statistics has been segmented, its segmentation parameters, e.g., defined regions are superimposed on or otherwise applied to the other image(s) to segment them. In this manner the segmentation process is performed once and the segmentation parameters are applied to an corresponding images.

A monitor 90 concurrently displays the aligned and commonly segmented Tc and Tl or other first and second isotope images. Optionally, an overlay processor 92 overlays 94 the segmented Tc and Tl images such that the monitor 90 concurrently displays 96 the two images superimposed, e.g., with differing color encodings.

If the data is acquired in a gated mode, a gated reconstruction is performed on the isotope imaging data with the best image statistics or the combined data. In a gated mode, the acquired data is segregated by cardiac phase or physiological motion position. For example, the cardiac cycle can be divided into 10 phases. The data from each phase can be reconstructed and attenuation, scatter, and collimator response corrected to generate an image of the heart in the corresponding cardiac phase. Because only a fraction of the data is in each phase, the above discussed segmentation issues for the isotope or energy levels with the worse noise statistics is magnified. The selected phase image with the best noise statistics or a selected phase image from combined data is again segmented and the segmentation parameters are applied to the selected phase image(s) from the other isotope(s).

The processor 70 further includes a motion estimator processor, program, algorithm, or other means 100 which estimates the movement or positional change among the gated phases. A motion correction processor, program, algorithm, or other means 102 generates motion correction parameters which are used in the image adjustment process 86 to perform a motion correction operation 104 concurrently on the first and second isotope images or can be fed back to the reconstruction processor 56 to re-perform reconstruction utilizing the motion parameters for inherent motion correction. The motion estimation parameters, for example, can be used to create a spatial transform to transform an image from one cardiac or physiological phase to another. For example, respiratory gated images can be spatially transformed into the end exhale phase. The motion correction parameters are determined from the image with the best noise statistics or the combined image in each phase. The motion correction parameters, e.g., spatial transform, are then applied to the other isotope image(s) in the same phase. Once the phase images for a given phase are transformed, all phase image for a given isotope are transformed into the same phase and combined. The motion parameters can also be fed back to the reconstruction processor to inherently correct for motion during reconstruction.

Although shown after orienting the heart in FIG. 2, it is to be appreciated that motion correction can be performed at other, particularly earlier, points in the process. In this manner, the gated isotope data from the individual or combined image windows with good noise statistics are used to gate and motion correct the image data from the isotope whose statistics are too weak for gating and motion correction. The gating and motion correction can also be performed during reconstruction.

The motion estimation or the spatial correction transform can also be used to transform the segmentation parameters or defined regions from one phase to another. In this manner, the phase image reconstructed from the energy window(s) with the best noise statistics can be segmented and the segmentation parameters can be transformed and applied to the other phase images from the same isotope and to the other phase images of the other isotope.

Although a single processor 70 is illustrated as performing several functions or processes, it is to be appreciated that each function or process can be performed by a dedicated processor, ASIC, or the like. Moreover, the functions or processes can be shared in various ways and combinations among a plurality of processors.

In another embodiment, Tl-201 is used for rest perfusion followed by Tc-99m for the stress study. In another embodiment, the Tc-99m rest perfusion study is followed by a Tl-201 stress study. In another embodiment, Tc-99m is used for perfusion and I-123-BMIPP is used for metabolic measurement, both at rest, to get information about chronic ischemia or myocardial infarct and tissue viability. In another embodiment, a Tc-99m based stress perfusion test is followed within a short time (e.g., less than 4 hours) by a rest study combining a Tc-99m reinjection for redistribution and an I-123-BMIPP for ischemic memory measurement. In another embodiment, a Tc-99m-ECDG stress measurement for determining perfusion defects is followed within the short time by an I-123-BMIPP rest measurement for ischemic memory. In another embodiment, combinations of Tc-99m perfusion and I-123-MIBG synthetic innervation measurements are made. These techniques are not limited to cardiac SPECT. They can be applied to any multiple isotope SPECT imaging protocol/application where segmentation or motion correction is to be performed, as well as PET, functional MRI, and other "imaging" modalities.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method of imaging comprising:
in a single imaging session, concurrently acquiring first isotope imaging data from a first isotope tracer uptaken by a subject in a first state and first and second isotope data from the first isotope tracer and a second isotope tracer uptaken by the subject in a subsequent second state;
reconstructing the acquired imaging data to generate a first state image from the first isotope imaging data and a second state image from the second isotope imaging data;
segmenting, based on the image with better noise statistics, one of the first or second state images or a combined image reconstructed from both the first and second isotope imaging data to generate segmentation parameters;
applying the segmentation parameters to both of the first state image and the second state image; and
concurrently displaying the segmented first and second state images.

2. The method according to claim 1, further including prior to performing the concurrent acquiring step in the single imaging session:
injecting the first isotope tracer into the subject to be imaged;
waiting for a first isotope tracer uptake period;
after the first isotope tracer uptake period and with an imaging session, injecting the second isotope tracer into the subject; and,
waiting a second isotope tracer uptake period.

3. The method according to claim 2, wherein:
waiting for the first isotope tracer uptake period is performed with the subject in a rest state; and
waiting for the second isotope tracer uptake period is performed while the subject is in a stressed state.

4. The method according to claim 1, further including:
overlaying the segmented first and second isotope images in the display.

5. The method according to claim 1, wherein one of the first and second isotope tracers includes technetium (Tc) and the other of the first and second isotope tracers includes thallium (Tl).

6. A method of imaging, comprising:
concurrently acquiring first and second isotope imaging data from a first isotope tracer uptaken by a subject in a first state and a second isotope tracer uptaken by the subject in a second state;
reconstructing the acquired imaging data to generate a first state image from the first isotope imaging data and a second state image from the second isotope imaging data;
segmenting a one of the first or second state images which has better image statistics or a combined image reconstructed from both the first and second isotope imaging data to generate segmentation parameters;
applying the segmentation parameters to each of the first state image and the second state image;
concurrently displaying the segmented first and second state images;
applying a physiological or cardiac gating during the concurrent acquiring of the first and second isotope imaging data; and
motion correcting each of the first isotope imaging data and the second imaging data in accordance with the gating.

7. The method according to claim 1, further including:
finding the heart of the subject in the one of the state images with the better image statistics or the combined image;
based on the image with better image statistics, reorienting the first and second state images such that main axes of the heart are oriented in preselected directions.

8. An imaging system comprising:
a gantry which defines an imaging region;
one or more imaging data acquiring devices disposed around the imaging region to acquire the first and second isotope imaging data;
one or more processors programmed to perform the method according to claim 1;
a display which concurrently displays the first and second state images.

9. A non-transitory computer-readable medium carrying software for controlling a computer processor to perform the steps of:
reconstructing concurrently acquired energy imaging data into a first state image depicting an uptake of a first isotope tracer injected into a subject and second imaging data into a second state image depicting an uptake of a second isotope tracer injected into the subject after both a first isotope tracer uptake period after injecting the first isotope tracer and a second isotope tracer uptake period after injection of the second isotope tracer, the concurrently acquiring being performed in a single imaging;
segmenting a one of the first and second state images which has better image statistics or an image reconstructed from both the first and second imaging data to generate segmentation parameters; and
applying the segmentation parameters to each of the first state image and the second state image.

10. An imaging system comprising:
  a reconstruction processor that reconstructs concurrently acquired
    first isotope imaging data into a first state image depicting an uptake of a first isotope tracer injected into a subject, and
    second isotope imaging data into a second state image depicting an uptake of a second isotope tracer injected into the subject a first isotope tracer uptake period after injecting the first isotope tracer and a second isotope tracer uptake period before the concurrently acquiring of the first and second isotope imaging data, all of the reconstructed data being acquired in a single imaging session subsequent to the first and second isotope uptake periods;
  a segmenting processor that segments, based on the image with better noise statistics, one of the first and second state images or an image reconstructed from both the first and second isotope imaging data to generate segmentation parameters;
  an image adjustment processor that applies the segmentation parameters to each of the first state image and the second state image to generate a segmented first state image and a segmented second state image; and
  a display which concurrently displays the segmented first and second state images.

11. The diagnostic imaging system according to claim 10, further including:
  an image processor that overlays the segmented first and second images.

12. The diagnostic imaging system according to claim 10, wherein one of the first and second isotopes is technetium (Tc) and the other of the first and second isotopes is thallium (Tl).

13. A diagnostic imaging system, comprising:
  a reconstruction processor that reconstructs concurrently acquired first energy imaging data into a first image depicting an uptake of a first isotope tracer injected into a subject and second energy imaging data into a second image depicting an uptake of a second isotope tracer injected into the subject a first isotope tracer uptake period after injecting the first isotope tracer and a second isotope tracer uptake period before the concurrently acquiring of the first and second energy imaging data;
  a segmenting processor that segments a one of the first and second images which has better image statistics or an image reconstructed from both the first and second energy imaging data to generate segmentation parameters;
  an image adjustment processor that applies the segmentation parameters to each of the first isotope image and the second image to generate a segmented first isotope image and a segmented isotope image;
  a display which concurrently displays the segmented first and second images; and
  a motion correction processor or the reconstruction processor that utilizes motion estimates to correct for motion in each of the first energy imaging data and the second energy imaging data in accordance with cardiac or physiological gating applied during the concurrent acquisition of the first and second energy imaging data.

14. The diagnostic imaging system according to claim 10, further including:
  a processor that finds the heart in the one of the isotope images with the better image statistics or the combined isotope image;
  a reorientation processor that concurrently reorients the first and second isotope images such that main axes of the heart are oriented in preselected directions.

* * * * *